United States Patent
Burkett et al.

[11] Patent Number: 6,132,782
[45] Date of Patent: Oct. 17, 2000

[54] SYSTEM AND METHOD FOR DETERMINING COOKING SYSTEM MEDIUM

[75] Inventors: Douglas A. Burkett, Eaton; Robert W. Stirling, Dayton, both of Ohio

[73] Assignee: Henny Penny Corporation, Eaton, Ohio

[21] Appl. No.: 09/323,137

[22] Filed: Jun. 1, 1999

Related U.S. Application Data

[60] Provisional application No. 60/087,692, Jun. 2, 1998.

[51] Int. Cl.[7] .............................. A47J 27/00; G01N 33/00
[52] U.S. Cl. .............................. 426/231; 99/331; 99/337; 99/329 R; 426/233
[58] Field of Search .................................... 426/231, 233, 426/523; 99/331, 332, 333, 337, 329 R; 73/73

[56] References Cited

U.S. PATENT DOCUMENTS

| | | | |
|---|---|---|---|
| 4,372,980 | 2/1983 | Luebke et al. | 426/231 |
| 4,913,038 | 4/1990 | Burkett et al. | 99/331 |
| 5,544,567 | 8/1996 | Davis et al. | 99/337 |

*Primary Examiner*—George C. Yeung
*Attorney, Agent, or Firm*—Baker Botts L.L.P.

[57] ABSTRACT

A system and method for identification of a medium in a cooking vessel is disclosed. The system includes a cooking vessel, a heat source for heating a medium within the cooking vessel, and a temperature sensor within the cooking vessel for measuring the medium temperature. A process controller is in communication with the temperature sensor and controls the heat source, and includes a processing unit and a storage unit. Data is input to the process controller through an input unit, and the temperature sensor sends a signal representing the medium temperature to the process controller. The process controller controls the heat source and applies heat to the medium, and also monitors the medium temperature in order to determine whether the medium is substantially water. The method first determines the temperature of a medium in a cooking vessel and initiates a cool detection process if the temperature of the medium is less than a predetermined temperature. If the temperature of the medium is above at least a predetermined temperature, the warm detection process is initiated. Next, the method determines if the medium includes water and provides an alarm if the media is substantially water.

26 Claims, 6 Drawing Sheets

SYSTEM AND METHOD FOR DETERMINING COOKING SYSTEM MEDIUM

This application incorporates by reference, in its entirety, U.S. Provisional patent application Ser. No. 60/087,692, filed Jun. 2, 1998.

BACKGROUND OF THE INVENTION

1. Field of the Invention

The invention relates generally to systems and methods for determining the type of medium in cooking systems, such as a deep fat fryer.

2. Description of Related Art

Large capacity cooking devices (referred to herein as deep fat fryers, cookers, and the like) have been devised for cooking products in a heated or pressurized environment, or both. Such devices may include a cooking vessel, which may be filled with a cooking substance (e.g., oil or shortening) and heating devices surrounding or immersed in the vessel for heating the cooking substance. Food products to be cooked are placed in the vessel, either directly or possibly contained in a food product cooking container, and are cooked for a desired length of time.

Cooking devices may have several temperature control stages to effectively and efficiently heat a cooking substance. For instance, in "melt" mode, energy is pulsed into a solid or liquid cooking substance to heat it without burning it or scorching the cooking vessel. During "cook" mode, the temperature of the cooking substance may be thermostatically regulated to a cooking set-point temperature, so that heat may be applied for an extended period of time below the setpoint. These two stages may be separated by the melt exit temperature, which is the temperature at which the transition from melt mode to cook mode occurs.

After repeated use, these cooking devices require cleaning. For example, the cooking substance may be first be drained from the vessel, and the vessel filled with a cleaning substance. This cleaning substance may simply be water, or it may include detergents. A controller for the cooking device may include a "cleaning" mode, in which controlled amounts of heat are applied to the cleaning substance in order to effectively clean the cooking vessel. Once the vessel is cleaned, the cleaning substance is drained, and the vessel is again filled with a cooking substance.

Although the process of cleaning a cooking device is not particularly complex, problems may still arise. In particular, problems may arise with the application of too much heat to a cleaning substance, especially if the cleaning substance has a boiling point near that of water. If too much heat is applied to this cleaning substance, and the cleaning substance boils, the cooking vessel may be damaged by oxidation or overpressure. This may require the costly replacement of the cooking vessel, heating elements, or sensors. Further, if water or another cleaning substance is not properly drained from the cooking vessel before the cooking vessel is refilled, the cooking substance may be contaminated by the water or cleaning substance. Such contaminated cooking substances may not heat properly and may cause the food products to cook unevenly or inadequately. Further, such contaminated cooking substances may adversely affect the flavor or the food products.

Further, if the cleaning substance is drained from the cooking vessel and not filled with a cooking substance before a heating cycle is initiated, the cooking vessel may overheat, resulting in a risk of fire or equipment damage. In particular, the fryer may be damaged by such "dry firing."

If medium is substantially water, and allowed to reach boiling temperatures, boil over may overflow or boil over and out of the cooking vessel. This too may result in fire or equipment damage. Moreover, such cooking substance boil-over or overflow may result in increased facility maintenance costs, which may further cause a reduction in operating efficiency.

SUMMARY OF THE INVENTION

Therefore, a need has arisen for a system and method for determining a medium in a cooking vessel.

A technical advantage of the present invention is that the system and method accurately determines the cooking vessel medium. Another technical advantage of the present invention is that it determines the cooking vessel medium with a minimum number of temperature measurements and calculations.

In one embodiment of the invention, a system for identification of a medium in a cooking vessel is disclosed. The system includes a cooking vessel, a heat source for heating a medium within the cooking vessel, and a temperature sensor within the cooking vessel for measuring the medium temperature. A process controller is in communication with the temperature sensor and controls the heat source, and includes a processing unit and a storage unit. Data is input to the process controller through an input unit, and the temperature sensor sends a signal representing the medium temperature to the process controller. The process controller controls the heat source and applies heat to the medium, and also monitors the medium temperature in order to determine whether the medium includes water.

In another embodiment of the invention, a method for identification of a medium in a cooking vessel is disclosed. The method first determines the temperature of a medium in a cooking vessel and initiates a cool detection process if the temperature of the medium is less than a predetermined temperature. If the temperature of the medium is above at least a predetermined temperature, the warm detection process is initiated. Next, the method determines if the medium is substantially water and provides an alarm if the media is substantially water.

However, other objects, features, and advantages will be understood from the following detailed description of preferred embodiments of the invention, in connection with accompanying drawings.

BRIEF DESCRIPTION OF THE DRAWINGS

For a more complete understanding of the present invention, the needs satisfied thereby, and the features and advantages thereof, reference now is made to the following descriptions taken in connection with the accompanying drawings in which.

DETAILED DESCRIPTION OF PREFERRED EMBODIMENTS

Preferred embodiments of the present invention and their advantages may be understood by referring to FIGS. 1–4 like numerals being used for like corresponding parts in the various drawings.

Figure 1:
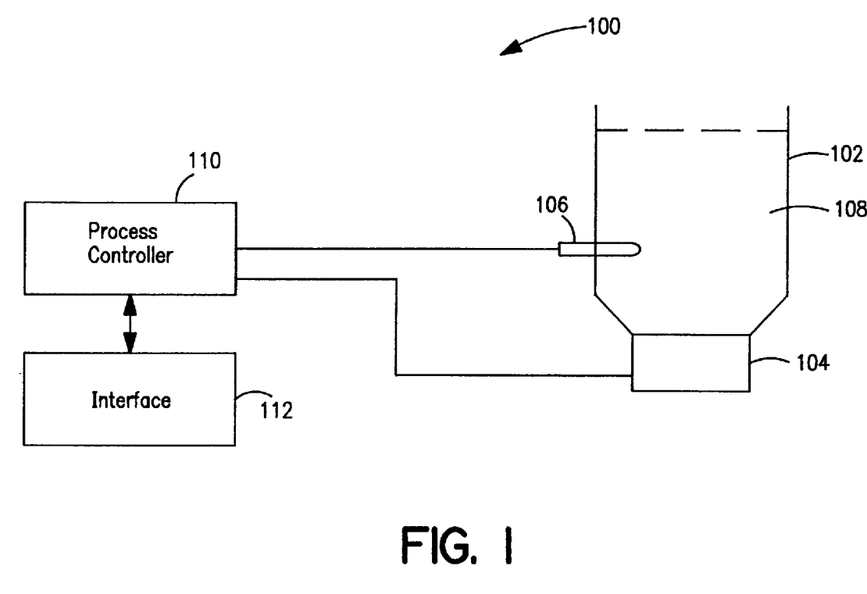
FIG. 1 depicts a schematic drawing of a cooking system according to an embodiment of the present invention.

FIG. 1 depicts a depicts a schematic drawing of a cooking system in a deep fat fryer according to an embodiment of the present invention. It will be understood by one of ordinary skill in the art that the present invention, which will be described below, may be readily implemented with various other fryer types and configurations and that the specific fryers in these figures are shown merely as preferred embodiments and for to purposes of illustration.

Referring to FIG. 1, a cooking system 100 is provided. Cooking system 100 includes a cooking vessel 102, which may be a deep fat fryer. Cooking vessel 102 includes a heat source 104 and a temperature sensor 106. Cooking vessel 102 may be filled with a medium 108. Medium 108 may be substantially water, a cooking substance, a cleaning substance, or mixtures thereof.

A temperature sensor 106 and heat source 104 are in communication with process controller 110. A suitable process controller 110 for cooking system 100 is a microprocessor, such as the MC68HC11 microcontroller, manufactured by Motorola, Inc. of Schaumburg, Ill. Other types of processors, such as a Pentium™-Series processor, manufactured by Intel Corporation of Santa Clara, Calif. may also be used.

Process controller 110 may also include a storage means (not shown). This may include magnetic media storage, RAM, or any suitable storage means. Data regarding the physical characteristics of water may be stored in storage means.

An operator interacts with cooking system 100 through user interface 112. User interface 112 may include an input means (not shown) and a display means (not shown). Suitable input means include a keypad, a touch-screen, a voice-recognition device, a plurality of input keys, or other input device that may be used to input relevant data into process control 110. Suitable display means may include a plurality of light emitting diodes (LEDs), a cathode-ray tube (CRT), a liquid crystal display (LCD), a multi-segment display, or other display that may be used to present information to an operator.

In an embodiment, an audible alarm (not shown) may be used to convey information to the operator. Buzzers, bells, chimes, or other sounds may be used to alert the operator of the status of cooking system 100. In another embodiment, a speaker is used to produce sounds for the operator. These may be human voice-simulating messages, or they may be pre-stored sounds Temperature sensor 106 may be any temperature sensing device capable of measuring the temperature of medium 108 within cooking vessel 102. In one embodiment, temperature sensor part no. DC32006AA-6-18, available from Durex Corporation, of Cary, Ill. may be used.

Temperature sensor 106 and process controller 110 are used to determine the type of medium 108 within cooking vessel 108. Specifically, in a first embodiment, temperature sensor 106 and process controller 110 are used to determine whether medium 108 in cooking vessel 102 comprises water, or if medium 108 does not comprise water, which includes mixtures of water and cooking substance.
Initial Medium Temperature Determination Referring to FIG. 2, in step 202, process controller 110 is initialized. This may include performing such functions as calibrating temperature sensor 106, initializing flags for process controller 110, setting default values, and the like. In step 204, temperature sensor 106 is used to measure the temperature of medium 108, $T_{MEDIUM}$. A signal representing the value of $T_{MEDIUM}$ may be sent to process controller 110. In step 205, process controller 110 determines whether the value of $T_{MEDIUM}$ is greater than a maximum expected temperature for a medium comprising substantially water, e.g., the maximum water temperature, $T_{WMAX}$. In one embodiment, $T_{WMAX}$ has a value of 220° F. If $T_{MEDIUM}$ is greater than $T_{WMAX}$, medium 108 in cooking vessel 102 is not substantially water, and in step 220, medium 108 is considered to not be substantially water.

Figure 2:
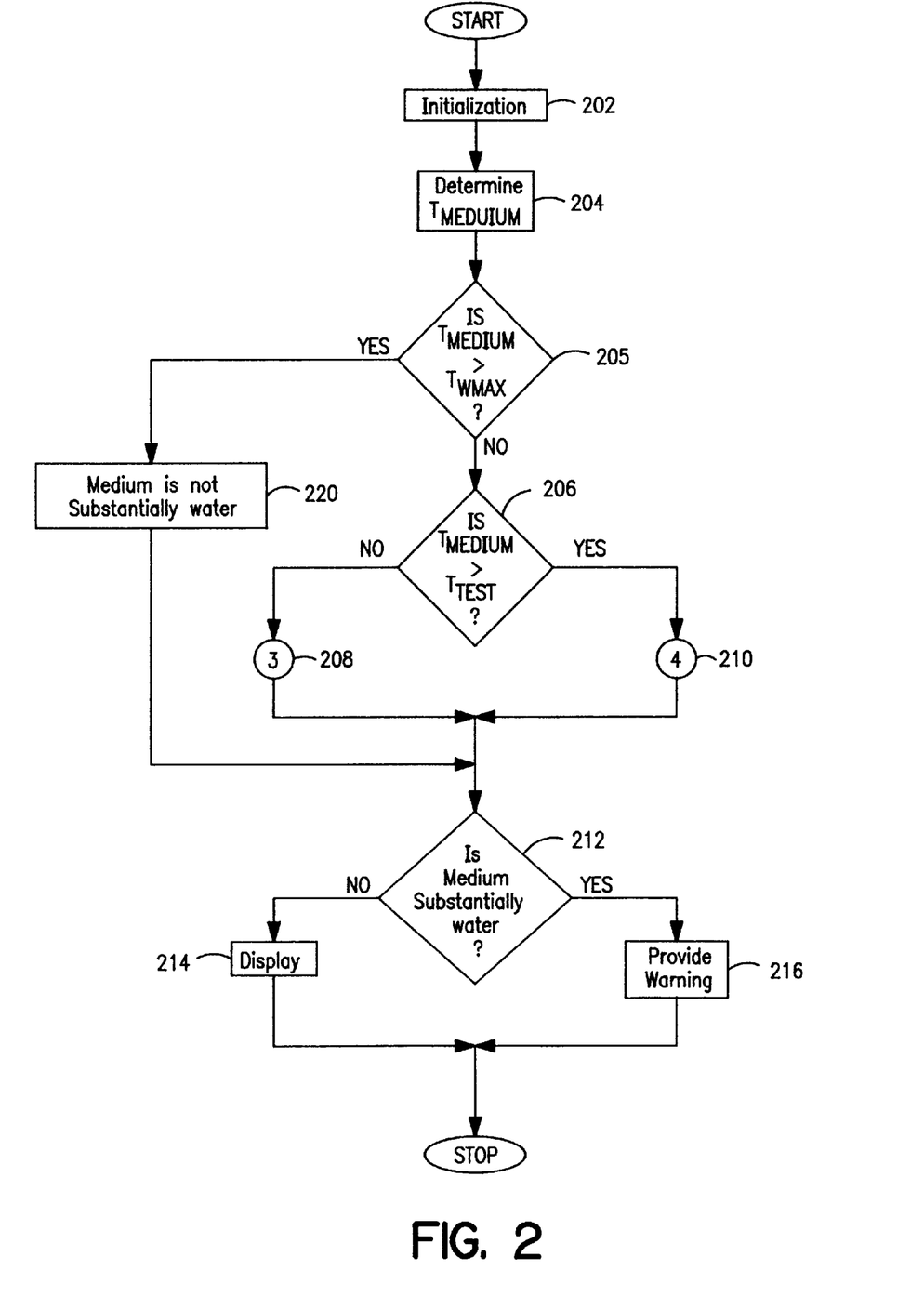
FIG. 2 is a flowchart depicting the frypot medium identification process according to a first embodiment of the present invention.
Figure 3A:
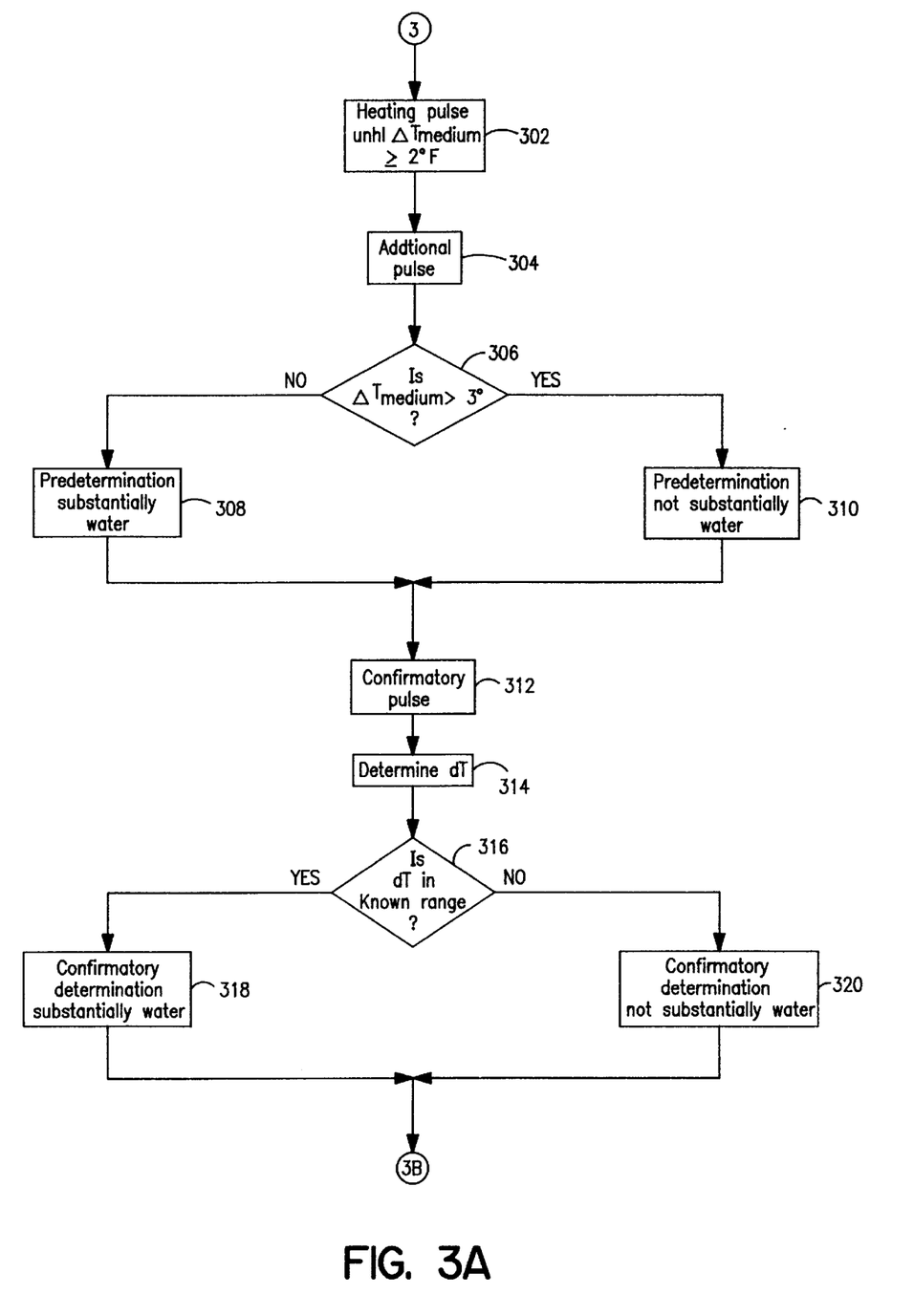
FIGS. 3a and b are flowcharts depicting the cool medium determination process according to a first embodiment of the present invention.
Figure 3B:
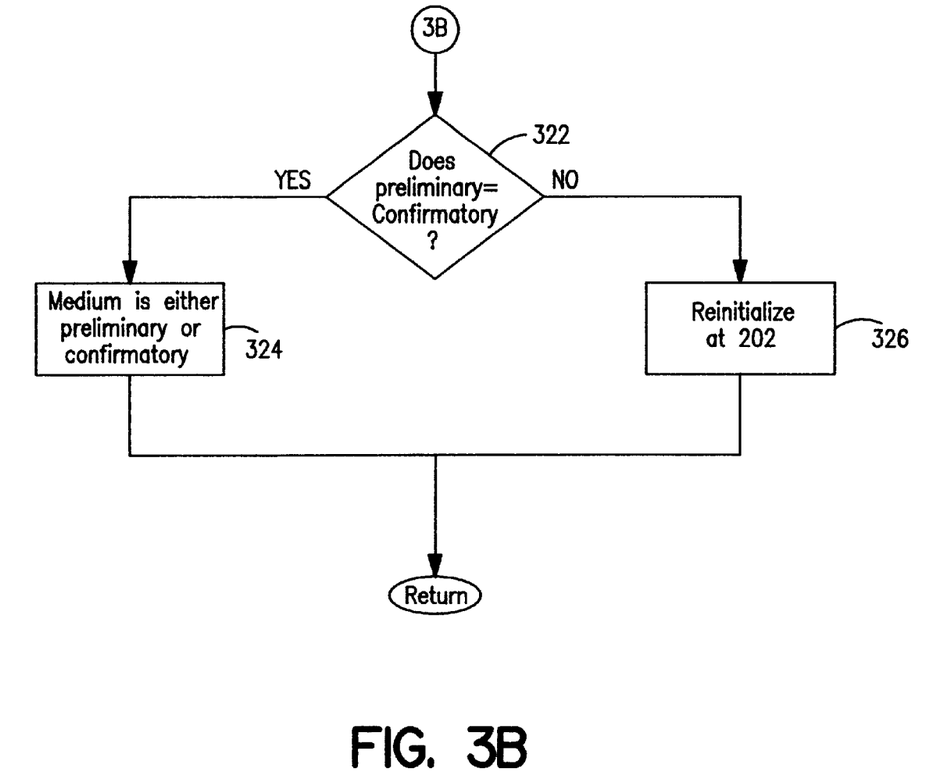

If $T_{MEDIUM}$ is less than $T_{WMAX}$, in step 206, process controller 110 determines whether or not the temperature of medium 108 is above or below a test temperature, $T_{TEST}$. In one embodiment, $T_{TEST}$ is set to 185° F. This temperature for $T_{TEST}$ is selected so that the temperature of medium 108 will, most likely, not be elevated above the boiling point of a medium comprising substantially water during the medium determination process described below. Any suitable temperature for $T_{TEST}$ that accomplishes this may also be used.
Cool Medium Determination Process If $T_{MEDIUM}$ is measured by temperature sensor 106 to be less than $T_{TEST}$, process controller 110 initiates the cool medium determination process. Referring to FIGS. 3a and b, in step 302, an initial series of heating pulses are provided to medium 108 by heat source 104. These heating pulses may include an "on" period, during which heat is applied to medium 108 by heat source 104, and an "off" period, during which heat is not applied to medium 108 by heat source 104. In one embodiment, a 40 second heating pulse having an "on" period of about 17 seconds followed by an "off" period of about 23 seconds may be used. Other durations and arrangements of "on" and "off" periods for the heating pulses may also be used.

The initial series of heating pulses may be provided until $T_{MEDIUM}$ is measured to change by at least a predetermined amount. The initial series of heating pulses may continue until $T_{MEDIUM}$ changes by at least 2° F. during the period of the heating pulse. Other appropriate temperature change values may also be used.

Next, in step 304, an additional heating pulse may be provided. This additional heating pulse may be the same type of heating pulse and duration as one of the initial heating pulses previously applied, or it may be a different type of pulse or it may have a different composition.

During the period of the additional heating pulse, in step 306, process controller 110 makes a preliminary determination of the type of medium 108 present in cooking vessel 102. This preliminary determination is made by measuring the rise of $T_{MEDIUM}$ during the period of the additional heating pulse. This may be accomplished using temperature sensor 106. Based on this measurement, a preliminary determination of whether medium 108 is substantially water may be made. In a first embodiment, in step 308, medium 108 may be considered not to be substantially water if $T_{MEDIUM}$ rises by at least 3° F. during the period of the additional heating pulse. Alternatively, in step 310, medium 108 is considered to be substantially water if $T_{MEDIUM}$ does not rise by at least 3° F. during the period of the additional heating pulse.

Once the preliminary determination is made, in step 312, at least one heating confirmatory pulse is provided by heat source 104 in order to determine the rate of rise in $T_{MEDIUM}$.

The rate of rise in $T_{MEDIUM}$ may be used to make a confirmatory determination of whether medium 108 is substantially water. In one embodiment, five consecutive confirmatory heating pulses, each of which may be similar to the heating pulses provided earlier, may be provided. Other numbers, types, and compositions of heating pulses may also be used.

In step 314, the rate of rise in $T_{MEDIUM}$ in response to these confirmatory heating pulses is determined. In order to determine the rate of rise of $T_{MEDIUM}$, first, $T_{MEDIUM}$ is measured immediately following the final heating pulse (temp$_2$). After the passing of predetermined time Δt, e.g., (150–250 seconds) the temperature of medium 108, (temp$_2$), is again measured. In one embodiment, a predetermined time of 200 seconds is used. The rate of rise, dt, of $T_{MEDIUM}$ may be determined by the equation:

$$dt = \frac{temp_2 - temp_1}{\Delta t} \quad (1)$$

Once the rate of rise dt in $T_{MEDIUM}$ is determined, in step 316, a confirmatory determination of the type of medium 108 is made. This determination is made by comparing the rate of rise dt to a know rate of rise for a medium substantially comprising water. Typical rates of rise dt for water are in the range of from about −0.0250° F./sec to about 0.100° F./sec under standard atmospheric pressure. If dt is within this range, medium 108 will have a confirmatory determination of being substantially water. If dt is not within this range, medium 108 will have a confirmatory determination of being not substantially water.

In step 322, process controller 110 compares the preliminary determination made in steps 308 and 310 to the confirmatory determination made in steps 318 and 320. If the preliminary determination and the confirmatory determination are the same (e,g., both identify medium 108 as substantially water), in step 324, process controller 110 considers the preliminary determination or the confirmatory determination to be an actual determination, and returns to step 212 in FIG. 2. If, in step 322, the preliminary and confirmatory determinations are not the same (e,g., one is substantially water and the other is not substantially water), in step 326, process controller 110 considers medium 108 to be undeterminable.

Process controller 110 may only allow a predetermined number of attempts to be made at determining whether medium 108 is substantially water before it considers medium 108 to be undeterminable. For example, in one embodiment, process controller 110 allows a total of three attempts at determining whether medium 108 is substantially water before it returns to step 202 of FIG. 2. Any suitable number of attempts may be used. If medium 108 is undeterminable, an audible or visible message or other means of indicating such to an operator may be provided.

Warm Medium Determination Process

Figure 4A:
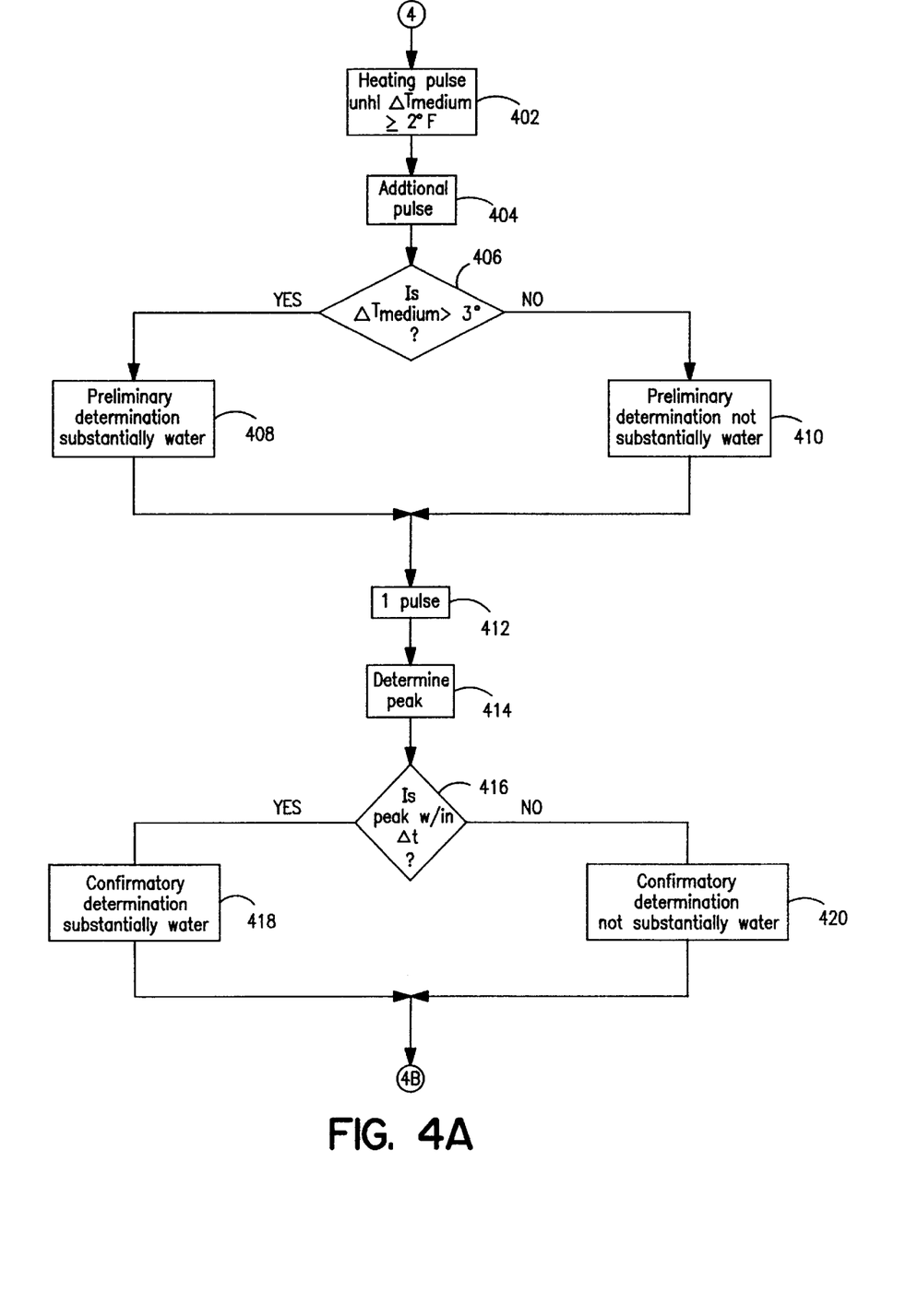
FIGS. 4a and b are flowcharts depicting the warm medium determination process according to a first embodiment of the present invention.
Figure 4B:
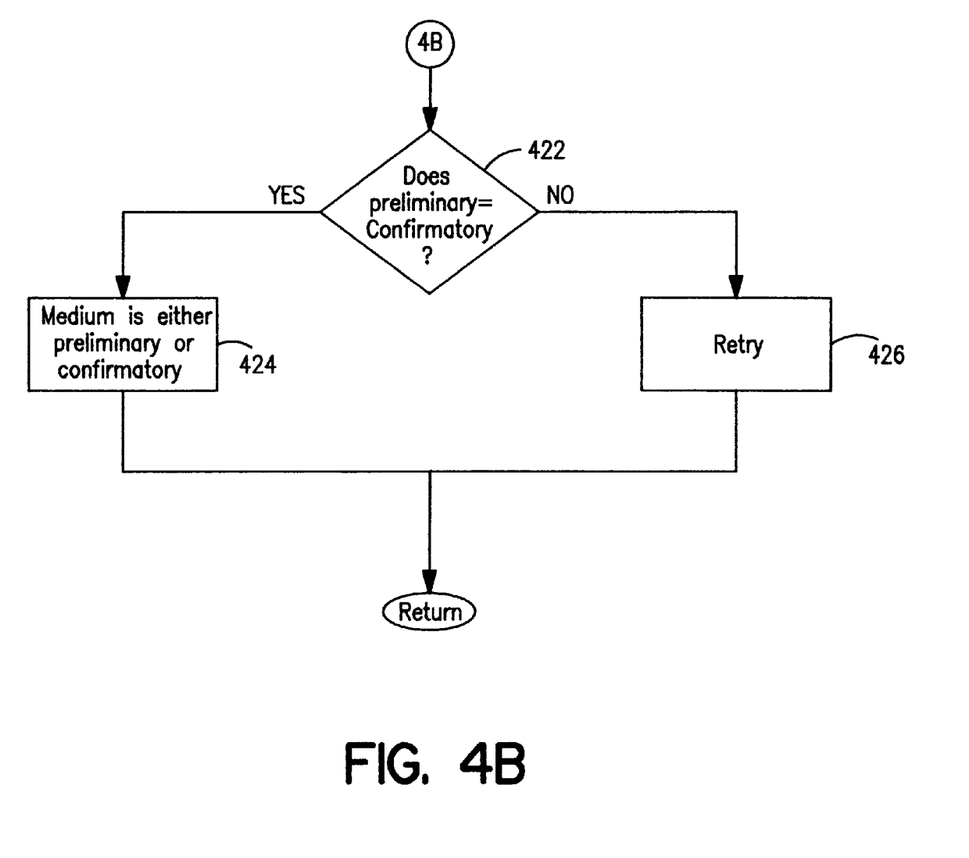

Referring again to FIG. 2, if, in step 206, $T_{MEDIUM}$ is measured by temperature sensor 106 as being greater than or equal to $T_{TEST}$, process controller 110 initiates the warm medium determination process. Referring to FIGS. 4a and b, in step 402, at least one initial heating pulse may be provided to medium 108 by heat source 104. The initial heating pulse may be the same as the heating pulses provided in step 302, or it may be a different type and duration of heating pulse.

The initial heating pulses are provided until $T_{MEDIUM}$ is measured to change by at least a predetermined amount. For example, in one embodiment, the initial heating pulses continue until $T_{MEDIUM}$ changes by at least 2° F. during the period of the heating pulse. Other appropriate temperature values may also be used.

Once $T_{MEDIUM}$ changes by at least a predetermined amount, an additional heating pulse may be provided in step 404. This additional pulse may be the same type of heating pulse and duration as one of the initial heating pulses previously applied, or it may be a different type of pulse or it may have different durations.

During the period of the additional heating pulse, in step 406, process controller 110 makes a preliminary determination whether medium 108 is substantially water.

This preliminary determination is made by measuring the rise of $T_{MEDIUM}$ during the "off" period during the period of the additional heating pulse. This may be accomplished using temperature sensor 106. Based on this measurement, a preliminary determination of whether medium 108 is substantially water may be made. For example, in one embodiment, in step 408, medium 108 is considered not to be substantially water if $T_{MEDIUM}$ rises by at least 3° F. during the period of the heating pulse. On the other hand, in step 410, medium 108 is considered to be substantially water if the $T_{MEDIUM}$ does not rise by at least 3° F. during the period of the heating pulse.

Once the preliminary determination is made, in step 412, a confirmatory heating pulse is provided. This confirmatory heating pulse may be the same type and duration as the initial heating pulse, or it may be different or it may have a different duration. After this confirmatory heating pulse is provided, in step 414, process controller 110 determines if $T_{MEDIUM}$ "peaks" within a predetermined period of time by measuring $T_{MEDIUM}$ with temperature sensor 106. A peak may be present when $T_{MEDIUM}$ falls by a predetermined amount. In one embodiment, a peak is present when $T_{MEDIUM}$ falls by at least 1° F. If a peak occurs within a predetermined period of time, in step 418, medium 108 will have a confirmatory determination of substantially water. If a peak does not occur within a predetermined period of time, in step 420, medium 108 will have a confirmatory determination of not substantially water.

In step 422, process controller 110 compares the preliminary determination made in steps 408 and 410 to the confirmatory determination made in steps 418 and 420. If the preliminary determination and the confirmatory determination are the same (e,g., both are substantially water), in step 424, process controller considers the preliminary or confirmatory determination to be the actual determination, and returns to step 212 in FIG. 2.

If, in step 422, the preliminary and confirmatory determinations are not the same (e,g., one is substantially water and the other is not substantially water), in step 426, process controller 110 repeats steps 412–422 at least one additional time. This may be repeated two times, for a total of three confirmatory determinations. If, at the completion of these repeated tests, the preliminary determination and confirmatory determination are still not the same, medium 108 may be considered to be undeterminable, and a message or other means of indicating this to the operator is provided.

Conclusion of Tests

Referring again to FIG. 2, if an actual determination is made, in step 212, if medium 108 is determined to be not substantially water, in step 214, a message may be displayed alerting the operator that the testing has been completed, and that cooking vessel 102 may now resume normal operation. This may be done audibly, or it may be done with a visual display means (not shown).

If, in step 212, medium 108 is determined to be substantially water, in step 216, a warning is provided. This may include an audible alarm, or it may be displayed on a visual display means (not shown). Further, process controller 110 may deactivate heat source 104, and thereby prevent or reduce any heat provided to medium 108, so that the temperature of medium 108 cools to ambient temperature. Further, controller 110 may prevent cooking system 100 from operating until the test is re-run and the presence of medium 108 being not substantially water is confirmed.

In another embodiment, a suitable message may be provided if medium 108 is undeterminable. If medium 108 cannot be identified as not substantially water, process controller 110 also may shut down cooking system 100 until medium 108 cools, and another attempt at identifying medium 108 is made.

An emergency override to bypass process controller 110 may be provided. This override permits the operator to circumvent process controller 110 after a determination of substantially water, and would allow cooking system 100 to operate. In another embodiment, the emergency override also may be used to override the bypass controller 110 when the identity of medium 108 is undeterminable.

In an alternate embodiment of the invention, the decision to pursue either the cool or warm medium determination process is made at the completion of the preliminary determination.

Process controller 110 may periodically check medium 108 for temperature disturbances. A temperature disturbance may be an abrupt change in $T_{MEDIUM}$ within a predetermined time period. For instance, in one embodiment, if $T_{MEDIUM}$ changes more than 2° Fahrenheit within 1 second, a temperature disturbance is considered to exist. Temperature disturbances may result from medium 108 being stirred, from additions or subtractions in the level or quantity of medium 108 or the like. In another embodiment, process controller 110 may constantly monitor medium 108 for temperature disturbances.

Process controller 110 may also evaluate temperature trending information. Process controller 110 may measure $T_{MEDIUM}$ once a second, and compares the current value $T_{MEDIUM}$ to the previous value $T_{MEDIUM-1}$. These comparisons may be stored in an array in order to determine temperature trends in medium 108. For example, if the value $T_{MEDIUM}$ is the same as $T_{MEDIUM-1}$, a value of "1" may be stored in the array for that second; if the value $T_{MEDIUM}$ is less than $T_{MEDIUM-}$, a value of "−2" may be stored in the array for that second; and, if the value $T_{MEDIUM}$ is greater than $T_{MEDIUM-1}$, a value of "2" may be stored in the array for that second. Other value and storage techniques may be used.

The temperature trending information may be stored for several seconds, as desired. In one embodiment, temperature trending information for three seconds may be stored. In other embodiments, there may be no limit to the amount of temperature trending information that may be stored.

By averaging the value of the temperature trending information, the trend of medium 108 may be determined. If the average of the temperature trending information is "1," then medium 108 has not changed in temperature. If the average of the temperature trending information is negative, medium 108 has decreased in temperature in the majority of the temperature trending information. If the average of the temperature trending information is positive, medium 108 has increased in temperature in the majority of the temperature trending information. This information may be used to evaluate disturbances in medium 108.

Other embodiments of the invention will be apparent to persons skilled in the relevant art from a consideration of this specification or practice of the invention disclosed herein. It is intended that the specification and examples be considered as exemplary only. Although a detailed description of the present invention is provided above, it is to be understood that the scope of the invention is not limited thereby, but is determined by the claims which follow.

We claim:

1. A system for identification of a medium in a cooking vessel comprising:

a cooking vessel;

a heat source for heating a medium within said cooking vessel;

a temperature sensor within said cooking vessel for measuring a temperature of said medium;

a process controller in communication with said temperature sensor for controlling said heat source, said process controller comprising:
   means for processing data; and
   means for storing said data;

input means for entering said data to said process controller;

wherein said temperature sensor sends a signal representing said measured medium temperature to said process controller, said process controller controls said heat source to apply heat to said medium, and said process controller monitors said temperature of said medium to determine whether said medium is substantially water.

2. The system for identification of a medium in a cooking vessel of claim 1, wherein said heat source provides heat to said medium in heating pulses.

3. The system for identification of a medium in a cooking vessel of claim 2, wherein said heating pulses are about 40 seconds in duration, and have an "on" time of about 17 seconds, and an "off" time of about 23 seconds.

4. The system for identification of a medium in a cooking vessel of claim 1, further comprising means for alerting an operator when said medium is substantially water.

5. The system for identification of a medium in a cooking vessel of claim 4, wherein said means for alerting an operator comprises a display means.

6. The system for identification of a medium in a cooking vessel of claim 4, wherein said means for alerting an operator comprises an audible means.

7. The system for identification of a medium in a cooking vessel of claim 1, further comprising means for overriding said process controller.

8. A method for identification of a medium in a cooking vessel comprising:

determining a temperature of a medium in a cooking vessel;

initiating a cool detection process if the temperature of said medium is less than a predetermined temperature;

initiating a warm detection process if the temperature of said medium is at least a predetermined temperature;

determining if said medium is substantially water; and providing an alarm responsive to a substantially water determination.

9. The method for identification of a medium in a cooking vessel of claim 8, wherein said predetermined temperature is 185° Fahrenheit.

10. The method for identification of a medium in a cooking vessel of claim 8, wherein said step of determining a temperature of a medium in a cooking vessel comprises:

measuring said temperature of said medium with a temperature sensor.

11. The method for identification of a medium in a cooking vessel of claim 8, wherein said cool detection process comprises:

provided a first series of heating pulses to said medium until the temperature of said medium changes by at least a predetermined amount;

providing a second heating pulse to said medium;

making a preliminary determination as to whether said medium is substantially water;

providing at least one third heating pulse to said medium;

determining a rate of rise of said medium; and making a confirmatory determination as to whether said medium is substantially water.

12. The method for identification of a medium in a cooking vessel of claim 11, further comprising:

comparing said preliminary determination to said confirmatory determination;

returning an actual result in response to said preliminary determination and said confirmatory determination being identical; and conducting reinitialization in response to said preliminary determination and said confirmatory determination not being identical.

13. The method for identification of a medium in a cooking vessel of claim 11, wherein said heating pulses are about 40 seconds in duration, and have an "on" time of about 17 seconds, and an "off" time of about 23 seconds.

14. The method for identification of a medium in a cooking vessel of claim 11, wherein five third heating pulses are provided.

15. The method for identification of a medium in a cooking vessel of claim 11, wherein said predetermined amount is 2° F.

16. The method for identification of a medium in a cooking vessel of claim 11, wherein said step of making a preliminary determination as to whether said medium is substantially water comprises:

measuring a rise in temperature of said medium following an on time of said second heating pulse;

assigning a preliminary determination of substantially water in response to said rise in temperature less than at least a predetermined rise; and assigning said preliminary determination of not substantially water in response to said rise in temperature greater than said predetermined rise.

17. The method for identification of a medium in a cooking vessel of claim 10, wherein said step of determining a rate of rise of said medium comprises:

measuring a first temperature of said medium;

measuring a second temperature of said medium after a predetermined time;

dividing the difference between said second temperature and said first temperature by said predetermined time.

18. The method for identification of a medium in a cooking vessel of claim 10, wherein said step of making a confirmatory determination as to whether said medium is substantially water comprises:

comparing said rate of rise of said medium with a known range for a rate of rise for a medium of substantially water;

assigning said confirmatory determination of water in response to a rate of rise within said known range for a rate of rise for said medium of substantially water; and assigning said confirmatory determination of other than water in response to a rate of rise greater than said known range of a rate of rise for said medium of substantially water.

19. The method for identification of a medium in a cooking vessel of claim 8, wherein said warm detection process comprises:

providing a first series of heating pulses to said medium until the temperature of said medium changes by at least a predetermined amount;

providing a second heating pulse to said medium;

making a preliminary determination as to whether said medium is substantially water;

providing at least one third heating pulse to said medium;

determining if the temperature of said medium reaches a peak within a predetermined time period; and making a confirmatory determination as to whether said medium is substantially water.

20. The method for identification of a medium in a cooking vessel of claim 19, wherein said heating pulses are about 40 seconds in duration, and have an "on" time of about 17 seconds, and an "off" time of about 23 seconds.

21. The method for identification of a medium in a cooking vessel of claim 19, wherein said predetermined temperature is 2° F.

22. The method for identification of a medium in a cooking vessel of claim 19, wherein said step of making a preliminary determination as to whether said medium is substantially water comprises:

measuring a rise in temperature of said medium following an on time of said second heating pulse;

assigning a preliminary determination of substantially water in response to said rise in temperature less than at least a predetermined rise; and assigning said preliminary determination of not substantially water in response to said rise in temperature greater than said predetermined rise.

23. The method for identification of a medium in a cooking vessel of claim 19, wherein said step of determining if the temperature of said medium reaches a peak within a predetermined time period comprises:

measuring said temperature of said medium for a predetermined time;

finding said peak when said temperature of said medium falls by at least one degree within said predetermined time.

24. The method for identification of a medium in a cooking vessel of claim 19, wherein said step of making a confirmatory determination as to whether said medium is substantially water comprises:

assigning said confirmatory determination of substantially water in response to a finding of said peak within said predetermined amount of time; and assigning said confirmatory determination of not substantially water in response to not finding said peak within said predetermined amount of time.

25. The method for identification of a medium in a cooking vessel of claim 19, further comprising:

comparing said preliminary determination to said confirmatory determination; and returning a positive result in response to said preliminary determination and said confirmatory determination being identical.

26. The method for identification of a medium in a cooking vessel of claim 19, wherein if said temperature of said medium is greater than a maximum water temperature, said medium is considered to not be substantially water.

* * * * *